US012605136B2

(12) United States Patent
Lin et al.

(10) Patent No.: US 12,605,136 B2
(45) Date of Patent: Apr. 21, 2026

(54) SUBCUTANEOUS AND CONTINUOUS BLOOD PRESSURE MONITORING

(71) Applicant: The Regents of the University of California, Oakland, CA (US)

(72) Inventors: Liwei Lin, Berkeley, CA (US); Yande Peng, Berkeley, CA (US); Sedat Pala, Berkeley, CA (US); Zhichun Shao, Berkeley, CA (US)

(73) Assignee: The Regents of the University of California, Oakland, CA (US)

( * ) Notice: Subject to any disclaimer, the term of this patent is extended or adjusted under 35 U.S.C. 154(b) by 28 days.

(21) Appl. No.: 18/432,053

(22) Filed: Feb. 5, 2024

(65) Prior Publication Data

US 2024/0206843 A1    Jun. 27, 2024

Related U.S. Application Data

(63) Continuation of application No. PCT/US2022/041868, filed on Aug. 29, 2022.

(60) Provisional application No. 63/240,843, filed on Sep. 3, 2021.

(51) Int. Cl.

| | |
|---|---|
| *A61B 8/04* | (2006.01) |
| *A61B 8/00* | (2006.01) |
| *A61B 8/12* | (2006.01) |
| *B06B 1/06* | (2006.01) |
| *H10N 30/06* | (2023.01) |
| *H10N 30/076* | (2023.01) |
| *H10N 30/079* | (2023.01) |

(52) U.S. Cl.
CPC .................. *A61B 8/04* (2013.01); *A61B 8/12* (2013.01); *A61B 8/4494* (2013.01); *B06B 1/0666* (2013.01); *H10N 30/06* (2023.02); *H10N 30/076* (2023.02); *H10N 30/079* (2023.02); *B06B 2201/76* (2013.01)

(58) Field of Classification Search
CPC ........... A61B 8/04; A61B 8/12; A61B 8/4483; A61B 8/4494; B06B 1/0666; B06B 2201/76; H10N 30/06; H10N 30/076; H10N 30/079
See application file for complete search history.

(56) References Cited

U.S. PATENT DOCUMENTS

| | | |
|---|---|---|
| 2018/0154393 A1 | 6/2018 | Viegas et al. |
| 2018/0256905 A1 | 9/2018 | Francia et al. |

OTHER PUBLICATIONS

International Search Report for PCT/US22/41868, 8 pages (Jan. 9, 2023).

*Primary Examiner* — Michael T Rozanski
(74) *Attorney, Agent, or Firm* — Richard Aron Osman

(57) ABSTRACT

A subcutaneous continuous blood pressure monitor system based on piezoelectric micromachined ultrasonic transducers (PMUTs) provides remote, silent and continuous monitoring solutions for the BP management.

1 Claim, 7 Drawing Sheets

Si    Mo    Al    AlN    SiO₂

Al     AlN     Mo     Si     Low stress SiO₂     Thermal SiO₂

SUBCUTANEOUS AND CONTINUOUS BLOOD PRESSURE MONITORING

CROSS-REFERENCES TO RELATED APPLICATIONS

This application is a continuation of PCT/US22/41868; filed: Aug. 29, 2022, which claims priority to U.S. Provisional Application No. 63/240,843; filed: Sep. 3, 2021, the disclosures of which are hereby incorporated by reference in its entirety for all purposes.

INTRODUCTION

Hypertension is a major precursor to cardiovascular disease and death. Current blood pressure (BP) monitoring systems based on cuff devices are cumbersome without the capability of continuously observing the BP, while researchers have demonstrated circadian blood pressure profiles can effectively reduce cardiovascular risks [1]. For example, lowering BP 10 mmHg translates to a 41% reduction in stroke [2]. Despite the great importance of BP monitoring and considerable medical cost spent in hypertension and related disease [3], there has not been a reliable system for monitoring BP continuously and comfortably yet. It is estimated that 45% of all strokes are attributed to uncontrolled hypertension and adequate control of BP carries the highest benefit in reducing stroke burden. Here, we disclose a subcutaneous continuous BP monitor system based on with piezoelectric micromachined ultrasonic transducers (PMUTs), providing remote, silent and continuous monitoring solutions for the BP management.

SUMMARY OF THE INVENTION

We disclose subcutaneous continuous BP monitor systems and devices based on PMUTs, which provides remote, silent and continuous monitoring solutions for BP management.

In an aspect the invention provides a novel subcutaneous, continuous blood pressure monitor (CBPM) that can continuously measure BP day and night, and prevent costly adverse events through earlier identification and notification of elevated BP and subsequent intervention to lower BP. An additional advantage is to reduce medication waste through faster optimization of medications. Automatic and seamless electronic monitoring of BP in addition to physician-defined thresholds for notification to allow intervention and patient-specific motivational strategies to encourage adherence. This creates earlier awareness of BP control status and subsequent earlier intervention. Earlier intervention can include proven strategies such as engaging support networks, gamification, or other patient-specific motivational approaches. By providing awareness of risk and leveraging the psychology of human behavior, in invention improves patient compliance to medication.

In an aspect the invention provides subcutaneous blood pressure monitoring systems and devices with piezoelectric micromachined ultrasonic transducers (PMUTs). Compared to the state-of-art, three distinctive achievements have been demonstrated: (1) precision and continuous measurements of the pressure (BP) from the diameter changes as small as 2.3 um by ultrasonic detections of a blood vessel; (2) experimental validations in both in vitro artery models and an acute animal study; and (3) first continuous and silent blood pressure monitoring system without a cuff, deploying implantable system based on MEMS technologies.

In embodiments:

the PMUTs are aluminum nitride (AlN)-based; and/or
the system or device is disposed subcutaneously in a person or other mammal.

In an aspect the invention provides a method of subcutaneous and continuous blood pressure monitoring comprising, continuously monitoring blood pressure of a person or other mammal with a disclosed subcutaneous blood pressure monitoring system or device.

The invention encompasses all combinations of the particular embodiments recited herein, as if each combination had been laboriously recited.

DESCRIPTION OF PARTICULAR EMBODIMENTS OF THE INVENTION

Unless contraindicated or noted otherwise, in these descriptions and throughout this specification, the terms "a" and "an" mean one or more, the term "or" means and/or. It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

Figure 1:
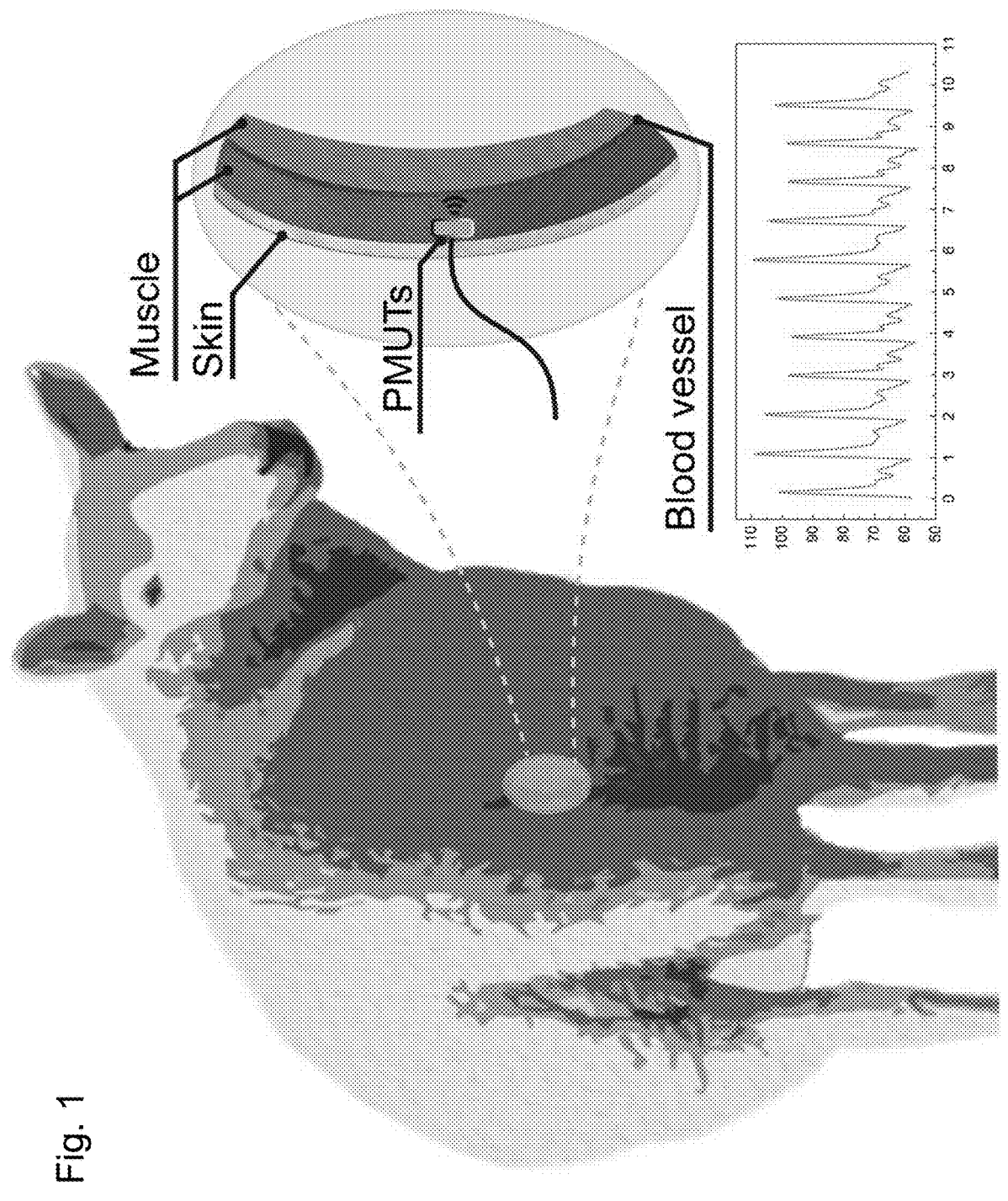
FIG. 1: Continuous and silent blood pressure monitoring based on PMUTs; blood pressure is graphed as mmHg vs. time (s).
Figures 2A, 2B:
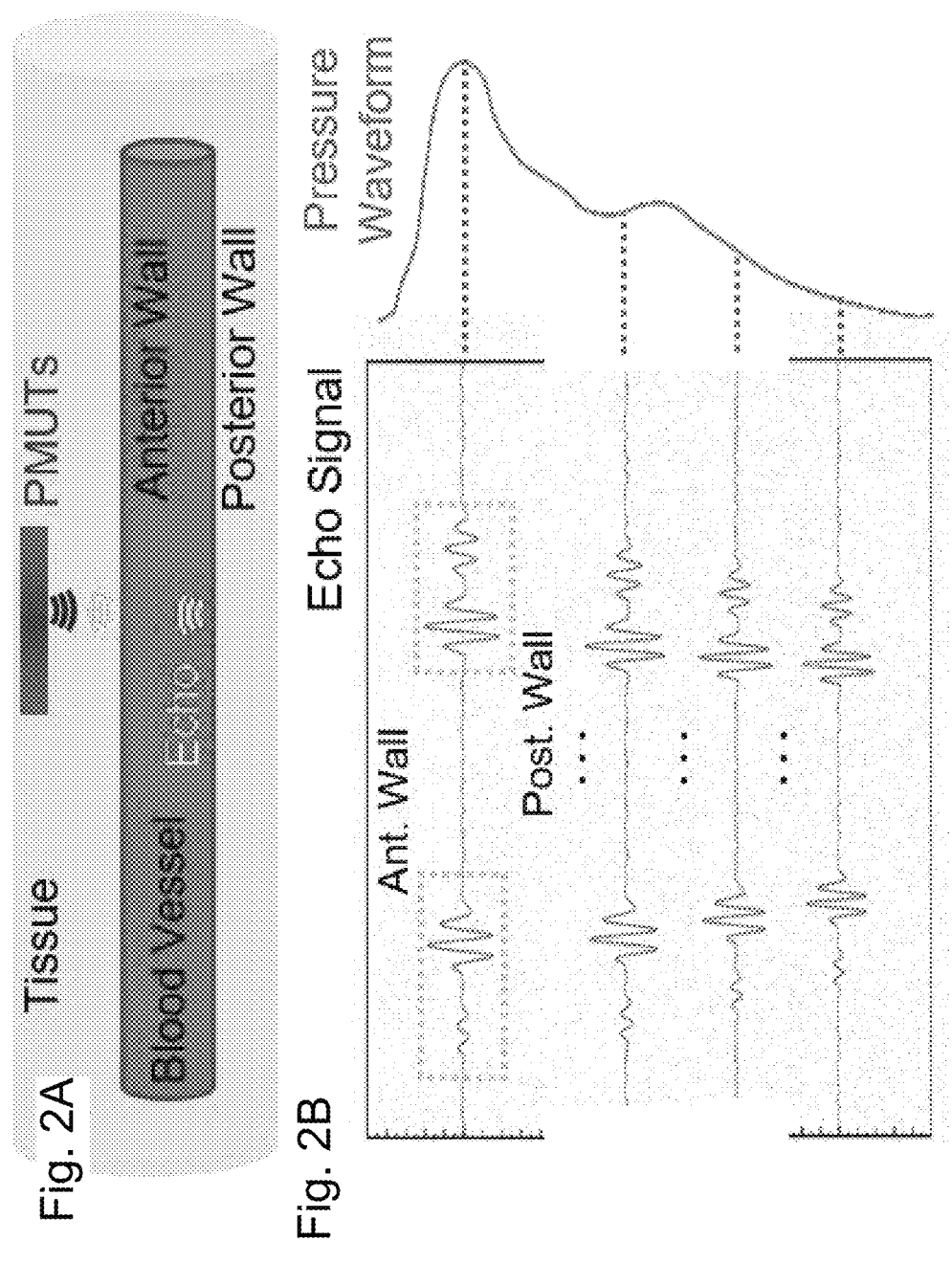
FIGS. 2A-2B: Working principle of the PMUTs BP monitor. A) pulse-echo method for artery diameter measuring; B) Correlation between artery diameter and blood pressure.

The concept of the continuous and silent BP monitoring is illustrated in FIG. 1. PMUTs is chosen as the sensor due to their advantage of miniaturization, good acoustic coupling, low-cost and low power consumption [4]. The small size of PMUTs enables implantable devices to measure the real-time BP inside the body of patients. Measurement results can be collected without using a cuff and transmitted to external receivers such as a mobile phone and other cloud centers for real-time diagnostics. FIGS. 2A-B describes the working principle based on the artery diameter changes due to the corresponding BP [5]. Specifically, ultrasonic waves can generate echoes at the artery-blood interfaces due to varying acoustic impedances and the TOF (Time-Of-Flight) interval between the echoes is utilized to characterize the diameter of the artery as:

$$p(t) = p_d \times e^{\beta\left(\frac{D(t)}{D_d}-1\right)}$$

Where the $p_d$, $D_d$ and $\beta$ are the diastolic pressure (which can be acquired on the brachial artery using a BP cuff), diastolic arterial diameter, and vessel stiffness, respectively. The BP waveform can then be obtained through such repetition to get the systolic and diastolic pressure of the patient.

Experimental Results

Figures 3A, 3B:
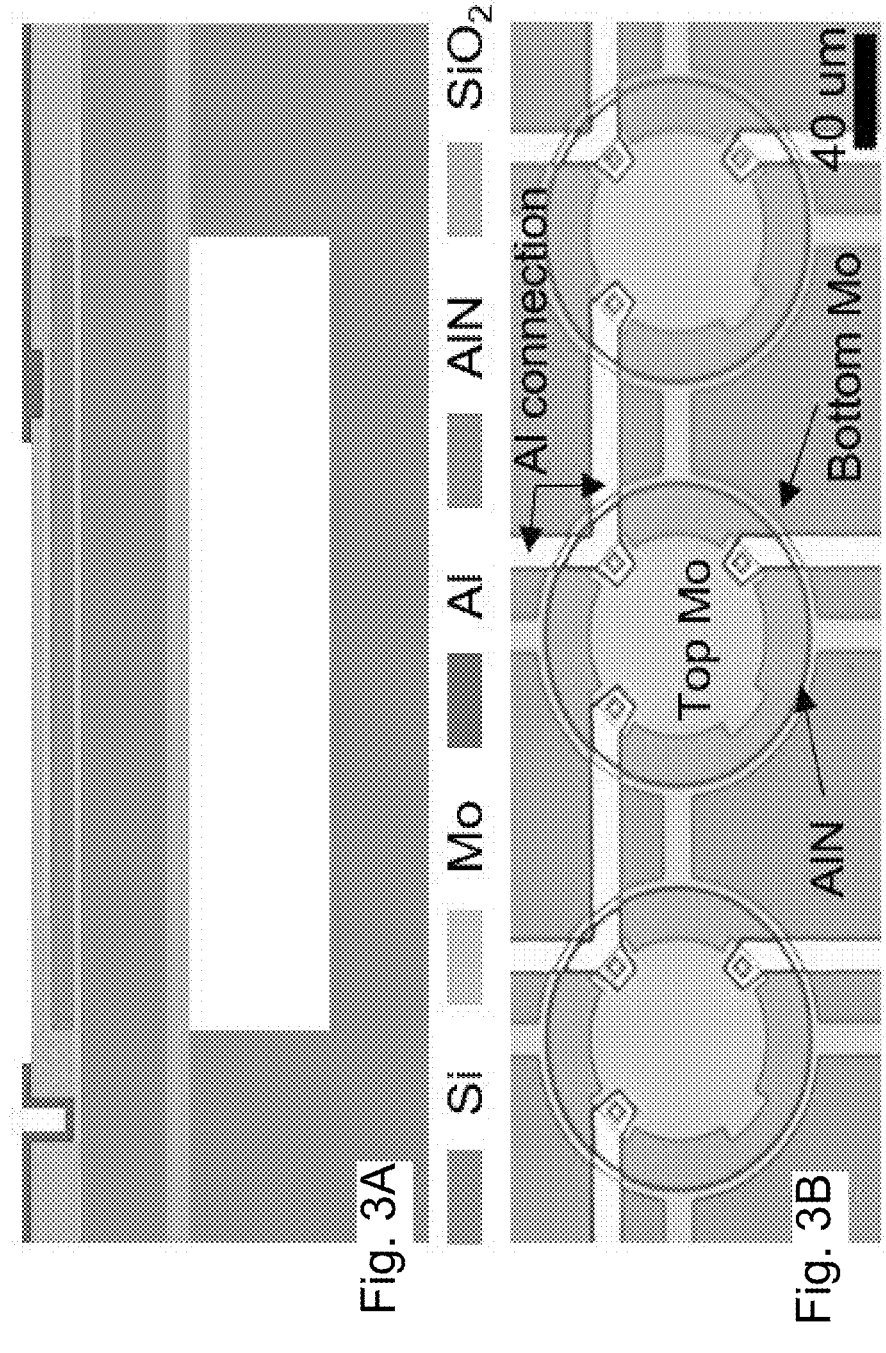
FIGS. 3A-B: A) Cross-section view and B) optical image of the PMUTs array.
Figures 4A, 4B, 4C, 4D, 4E, 4F, 4G:
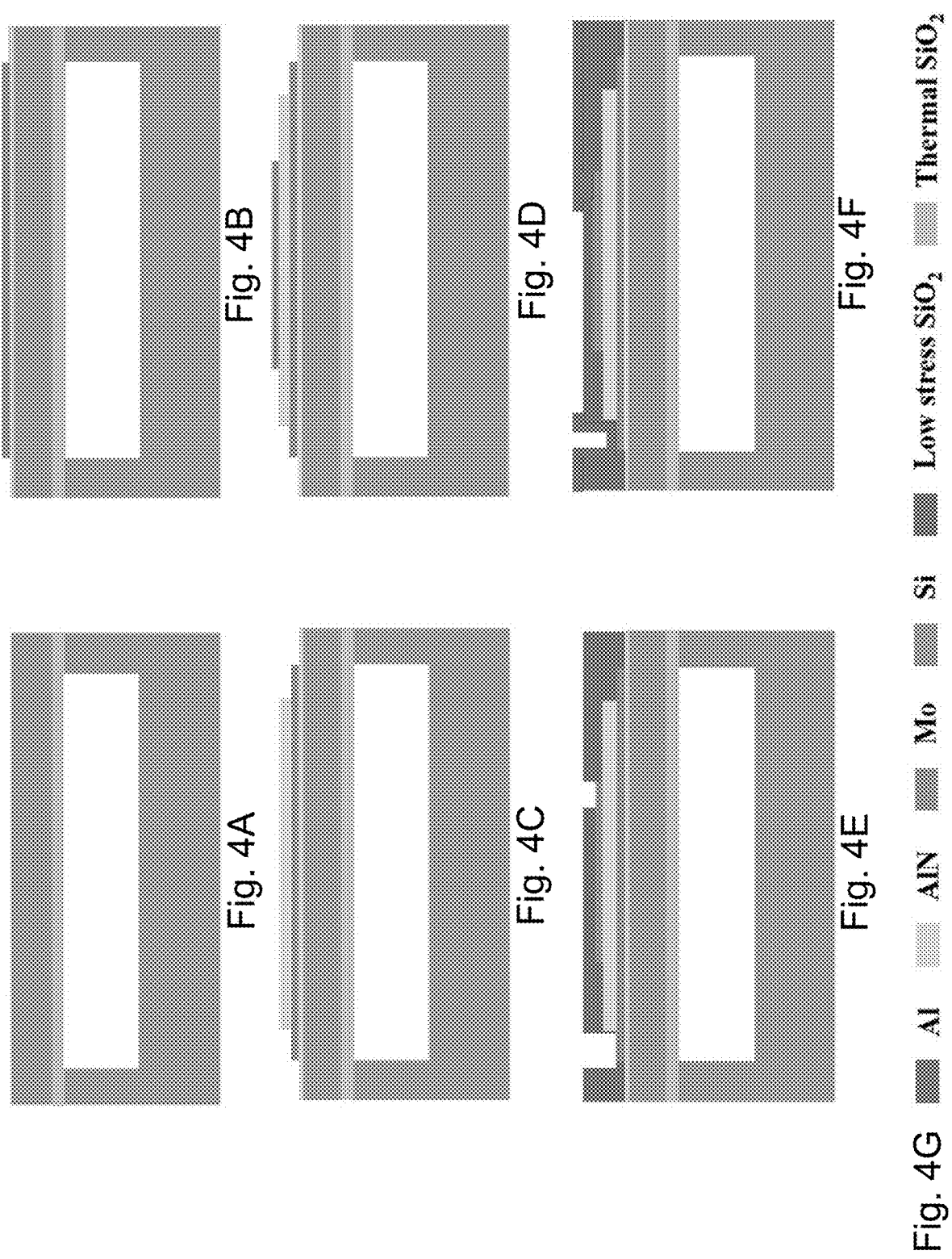
FIGS. 4A-G: The fabrication process of the pMUTs array. (A) The bare silicon wafer with a predefined cavity directly bonded to another SOI wafer. (B) Bottom Mo deposited and patterned. (C) AlN deposited and patterned. (D) Top Mo deposited and patterned. (E) Dielectric layer SiO2 deposited and patterned. (F) Top Al connection lines and pads deposited and patterned. (G) Legend.

The PMUTs array is based on AlN (FIG. 3A) fabricated from a cavity-SOI (silicon-on-insulator) process [6] and the radius of the diaphragm is 50 μm (FIG. 3B). The fabrication process of the pMUTs array starts from a cavity silicon-on-insulator (SOI) wafer, which is formed via etching cavities on a silicon substrate, then bonding the handled wafer with a 5 μm structure silicon wafer in vacuum (FIG. 4A). The cavities are 280 μm in diameter and 20 μm in depth, and define the location of the pMUTs. Then, 20 nm aluminum nitride (AlN) seeds are deposited by atomic layer deposition (ALD) to optimize deposition condition of the functional AlN piezoelectric layer (FIG. 4B). Next, 0.2 μm bottom molybdenum (Mo), 1 μm AlN and 0.2 μm top Mo are deposited by sputtering and patterned using $SiO_2$ as hard masks (FIGS. 4B-D). After a dielectric layer of 0.2 μm $SiO_2$ is deposited by plasma enhanced chemical vapor deposition (PECVD) and patterned to open the top-to-top via (FIG. 4E), the top Al connection lines and pads with thickness of 0.7 μm are deposited and patterned (FIG. 4F). [6] FIG. 4G is the legend for FIGS. 4A-F.

Figures 5A, 5B:
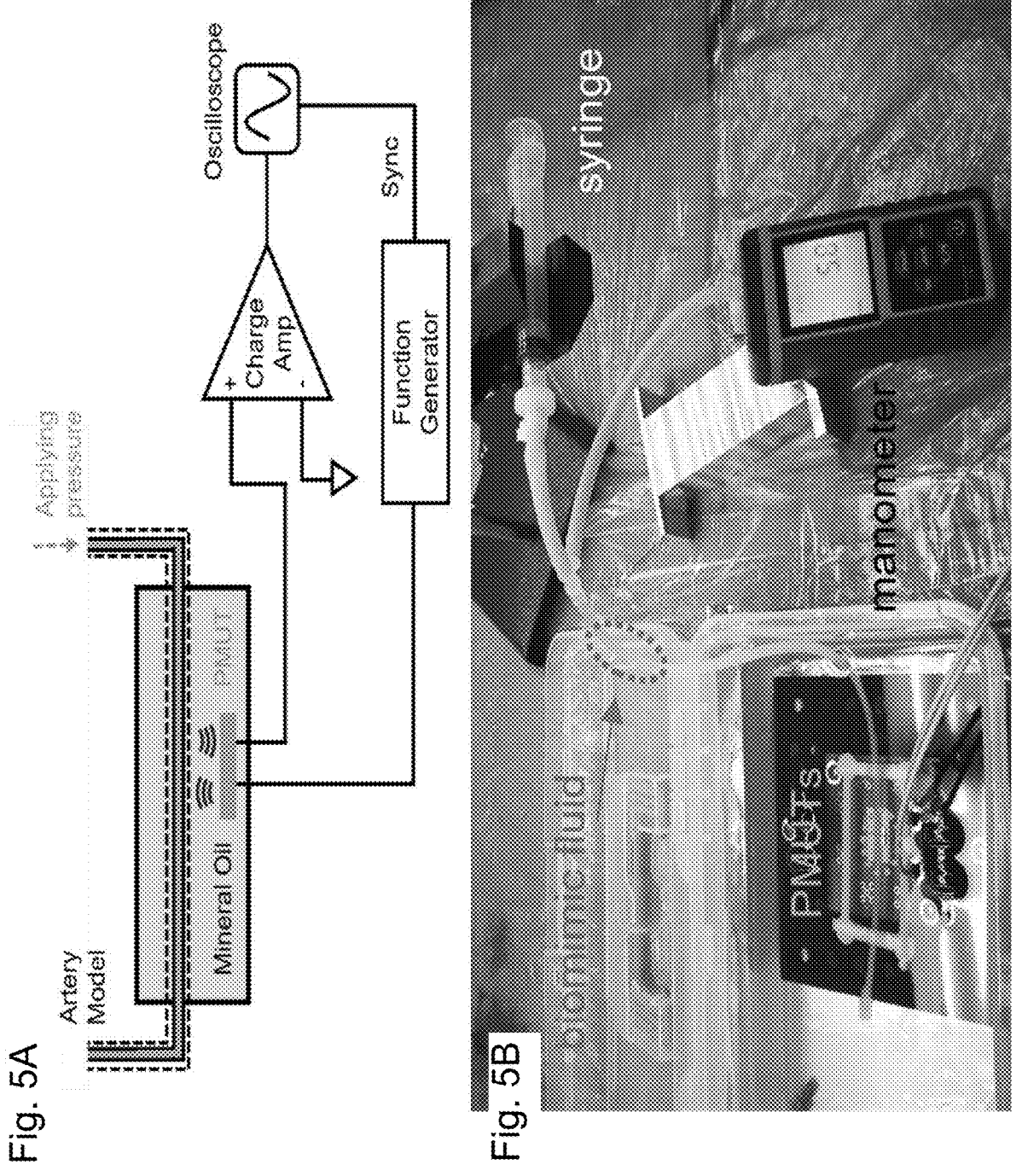
FIGS. 5A-B: A) Illustration of the overall block diagram; B) the in vitro experimental setup.
Figures 6A, 6B, 6C:
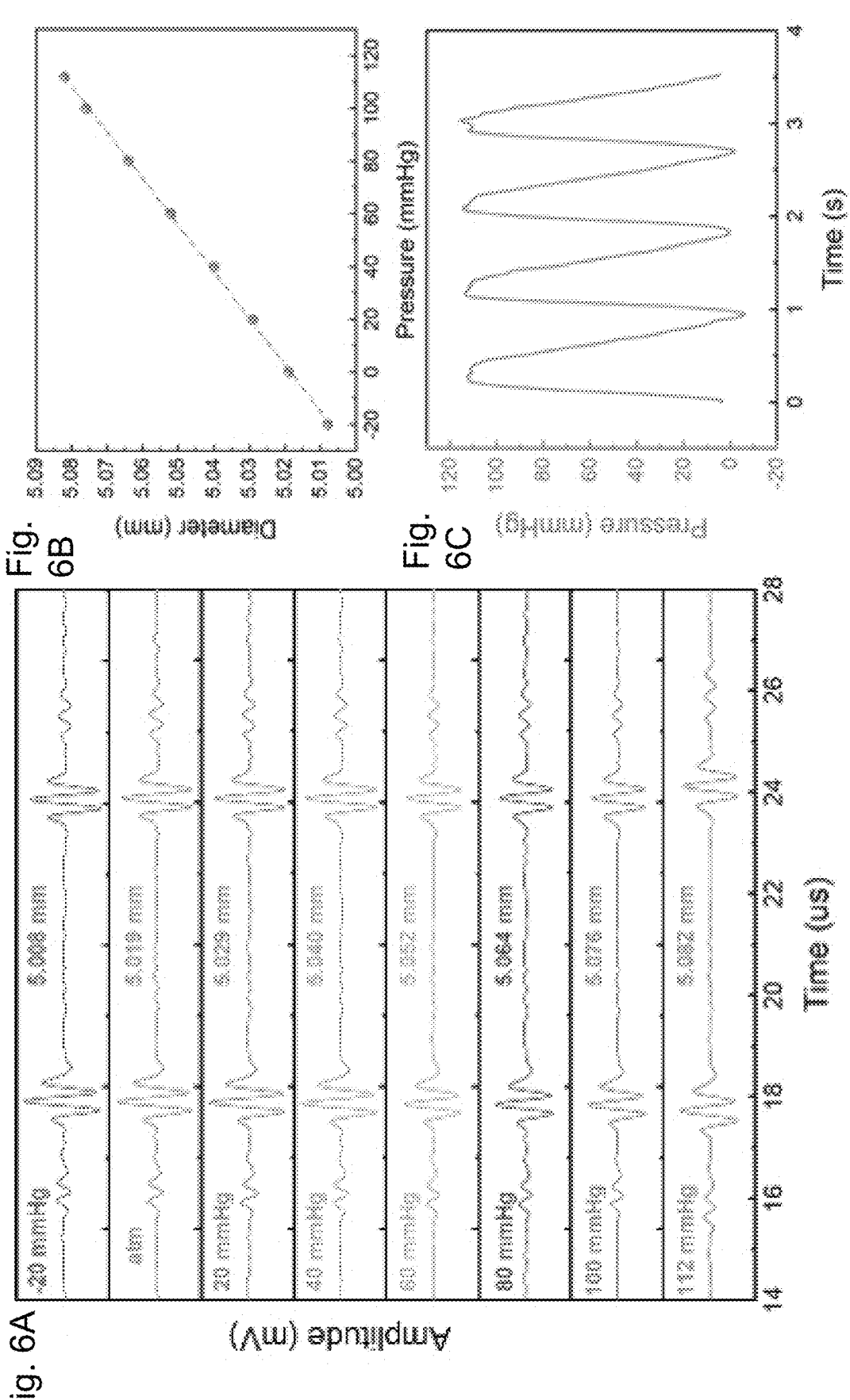
FIGS. 6A-C: A) Echo signal under different pressure applied; B) correlation between diameter and pressure; C) in vitro dynamic pressure waveform.

The working principal is first validated by the in vitro experiments (FIGS. 5A-B). A silicone tube is used to emulate an artery with externally applied pressure. A pulse repetitive frequency of 1000 Hz is applied to capture a smooth waveform [5] while the echo signals are collected. FIG. 6A shows the waveforms with respect to different pressure and a larger time interval can be observed as a larger pressure is applied to expand the tube with calibrated correlation in FIG. 6B. The dynamic waveform is then obtained following this correlation by changing the pressure inside the tube continuously. Results show good correspondence in terms of both frequency and magnitude (FIG. 6C).

Figures 7A, 7B, 7C:
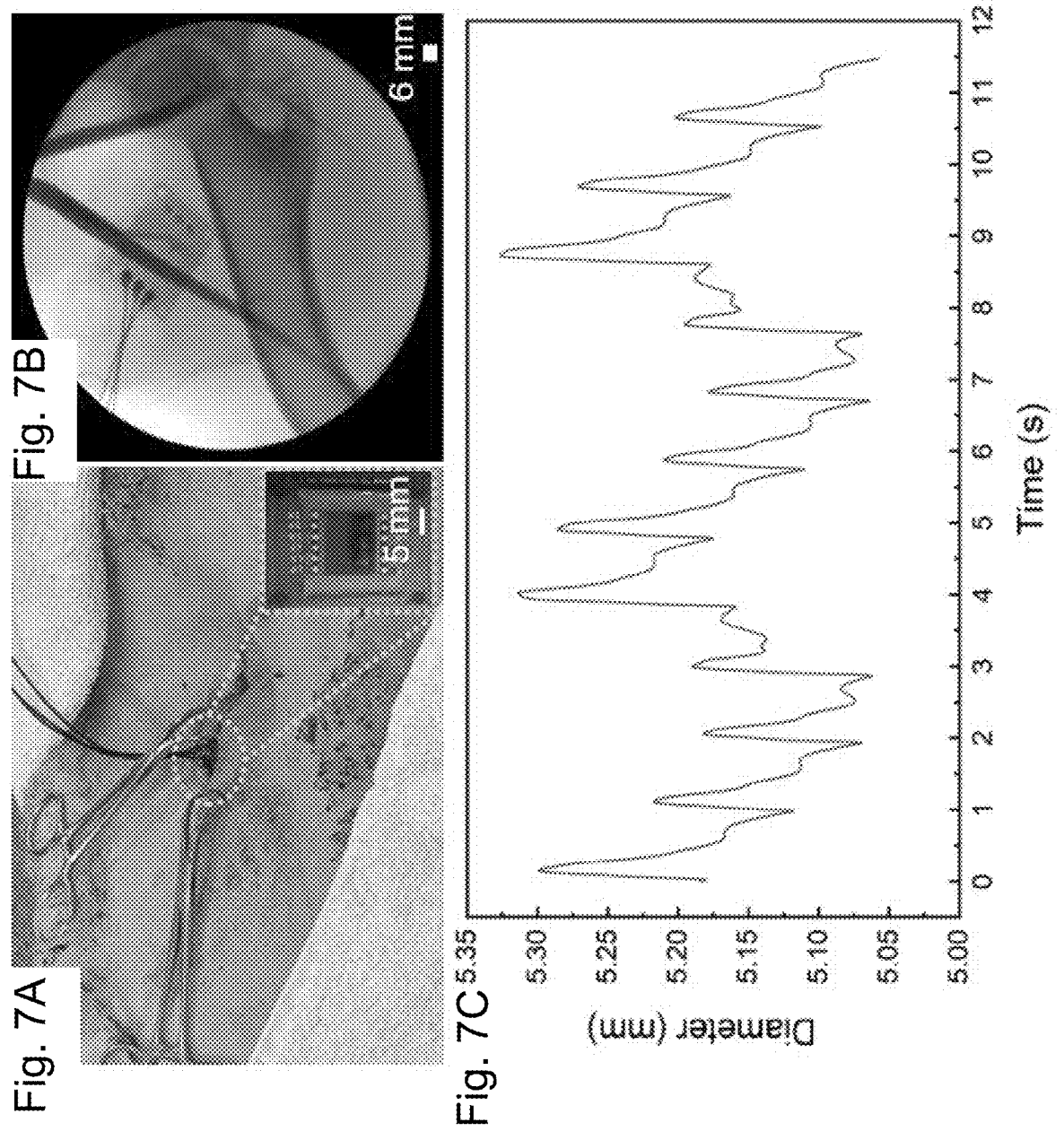
FIGS. 7A-C: Acute animal study. A) PMUTs sensors embedded in sheep; B) fluoroscopy of the PMUTs inside the sheep; C) in vivo artery diameter waveform.

Acute in vivo animal study is then conducted. As shown in FIG. 7A and FIG. 7B, the PMUTs sensor consisting of three 23*26 arrays is embedded into the sheep near its femoral artery. Collected waveforms (FIG. 7C) shows the typical cardiovascular cycles with components including dicrotic notch etc.

REFERENCES

[1] SPRINT Research Group, *NEJM*, 22 (2015), pp. 2103-2116.

[2] Hong, Kuen Sik. *Journal of Stroke*, 2017, 19(2):152-165.

[3] Demaerschalk. *Stroke (Am J Manag Care)*, 2010, 16 (7): 525-533.

[4] Akhbari, Sina et al., *Journal of Microelectromechanical Systems*, vol. 25, no. 2, pp. 326-336, 2016.

[5] Wang, Chonghe, et al., *Nature biomedical engineering*, 2.9 (2018), pp. 687-695.

[6] Chen, Xuying, et al. *Journal of Microelectromechanical Systems*, vol. 28, no. 4, pp. 707-716, 2019.

The invention claimed is:

1. A method of subcutaneous and continuous blood pressure monitoring comprising, continuously monitoring blood pressure of a person or other mammal with a subcutaneous, implantable blood pressure monitoring device with an array of piezoelectric micromachined ultrasonic transducers (PMUTs), configured for subcutaneous and continuous and silent blood pressure monitoring without a cuff, implanted in the person or the other mammal, wherein the PMUTs comprise a vacuum cavity silicon-on-insulator (SOI) water segment, and wherein:

the PMUTs comprise an aluminum nitride (AlN) piezoelectric layer;

the PMUTs comprise a round pressure sensing diaphragm having protruding tabs to facilitate electrical connections; and the PMUTs comprise from bottom to top molybdenum (Mo), AlN and Mo layers;

and wherein the device is configured, from bottom to top:

a) the vacuum cavity silicon-on-insulator (SOI) wafer segment;

b) the aluminum nitride (AlN) piezoelectric layer;

c) the molybdenum (Mo), AlN and Mo lavers;

d) a dielectric layer of $SiO_2$ patterned to open a top-to-top via; and e) Al connection lines and pada.

\* \* \* \* \*